US009510765B2

(12) United States Patent
Greder

(10) Patent No.: US 9,510,765 B2
(45) Date of Patent: Dec. 6, 2016

(54) DETECTION AND FEEDBACK OF INFORMATION ASSOCIATED WITH EXECUTIVE FUNCTION

(75) Inventor: Rod Greder, Pine City, MN (US)

(73) Assignee: Awear Technologies, LLC, Pine City, MN (US)

( * ) Notice: Subject to any disclaimer, the term of this patent is extended or adjusted under 35 U.S.C. 154(b) by 364 days.

(21) Appl. No.: 13/989,536

(22) PCT Filed: Nov. 23, 2011

(86) PCT No.: PCT/US2011/062109
§ 371 (c)(1),
(2), (4) Date: Sep. 18, 2013

(87) PCT Pub. No.: WO2012/071545
PCT Pub. Date: May 31, 2012

(65) Prior Publication Data
US 2014/0023999 A1    Jan. 23, 2014

Related U.S. Application Data

(60) Provisional application No. 61/417,107, filed on Nov. 24, 2010.

(51) Int. Cl.
*A61B 5/0482* (2006.01)
*A61B 5/16* (2006.01)
*A61B 5/00* (2006.01)

(52) U.S. Cl.
CPC .............. *A61B 5/0482* (2013.01); *A61B 5/16* (2013.01); *A61B 5/6803* (2013.01); *A61B 5/165* (2013.01); *A61B 5/167* (2013.01); *A61B 5/168* (2013.01)

(58) Field of Classification Search
CPC ..................................................... A61B 5/0482
(Continued)

(56) References Cited

U.S. PATENT DOCUMENTS 5,519,522 A * 5/1996 Fergason ................. B23K 9/32
                                                       219/147
5,731,766 A * 3/1998 Akamatsu .............. G01C 21/36
                                                       340/905

(Continued)

OTHER PUBLICATIONS

"International Application Serial No. PCT/US2011/062109, Search Report mailed Mar. 8, 2012", 2 pgs.
(Continued)

*Primary Examiner* — Robert J Utama
*Assistant Examiner* — Thomas Hong
(74) *Attorney, Agent, or Firm* — Schwegman Lundberg & Woessner, P.A.

(57) ABSTRACT

An example includes a neurosensing and feedback device to detect mental states and alert the wearer, such as in real-time. In an example, neural activity is detected by sensors that measure frequency, amplitude, synchrony, sequence and site of brain activity. These measurements can be compared to neural signatures and patterns shown to be correlated to neuropsychological conditions and disorders. When these measurements indicate an undesirable state the wearer is alerted via visual, audible or tactile means designed to be highly effective at alerting the wearer and allowing them to adjust their brain activity. Executive function, known to be crucial for school readiness, academic achievement and successful life outcomes, is the chief state to be detected, trained and supported. The device is designed to be used during primary activities, e.g. reading and listening, and to not require third party intervention during primary use.

19 Claims, 9 Drawing Sheets

(58) Field of Classification Search
USPC .......................................................... 434/236
See application file for complete search history.

(56) References Cited

U.S. PATENT DOCUMENTS

| | | | |
|---|---|---|---|
| 6,167,298 A * | 12/2000 | Levin | A61B 5/0482 600/545 |
| 6,456,438 B1 * | 9/2002 | Lee | G02B 27/01 359/630 |
| 6,511,175 B2 | 1/2003 | Hay et al. | |
| 2001/0050754 A1 * | 12/2001 | Hay et al. | 351/213 |
| 2005/0017870 A1 * | 1/2005 | Allison | G06F 3/015 340/4.13 |
| 2006/0252978 A1 | 11/2006 | Vesely et al. | |
| 2006/0273919 A1 * | 12/2006 | Sato | G09F 9/35 340/815.45 |
| 2007/0285759 A1 * | 12/2007 | Ash | B60J 3/04 359/275 |
| 2008/0062338 A1 | 3/2008 | Herzog et al. | |
| 2010/0085462 A1 * | 4/2010 | Sako | G02B 27/017 348/333.01 |
| 2010/0145215 A1 | 6/2010 | Pradeep et al. | |

OTHER PUBLICATIONS

"International Application Serial No. PCT/US2011/062109, Written Opinion mailed Mar. 8, 2012", 5 pgs.

* cited by examiner

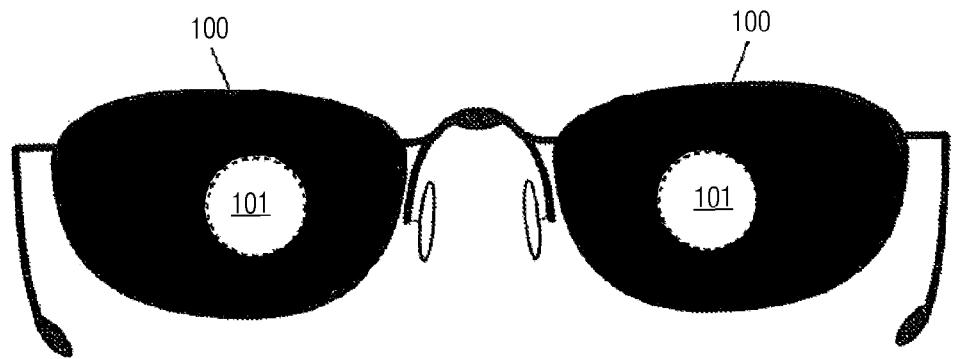
FIG.PAGE-
5A
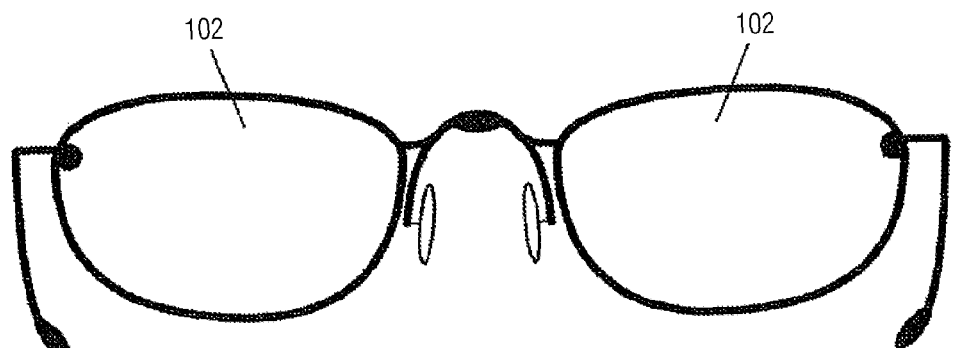
FIG.PAGE-
5B

DETECTION AND FEEDBACK OF INFORMATION ASSOCIATED WITH EXECUTIVE FUNCTION

CLAIM OF PRIORITY

This application is a U.S. National Stage Filing under 35 U.S.C. 371 of International Patent Application Ser. No. PCT/US 2011/062109, filed on Nov. 23, 2011, and published on May 31, 2012, as WO 2012/071545, which claims the benefit of priority to U.S. Patent Application Ser. No. 61/417,107, entitled "DEVICE TO DETECT AND NOTIFY WEARER OF MENTAL STATES IN REAL-TIME DURING REAL-WORLD TASKS," filed on Nov. 24, 2010, which are hereby incorporated by reference herein in their entirety.

TECHNICAL FIELD

The present subject matter relates to teaching, and more particularly to a device that combines neurosensing and feedback, such as on a mobile platform.

BACKGROUND

U.S. Pat. No. 6,097,981 to Freer discloses an apparatus and method with an electroencephalography ("EEG") based biofeedback system wherein a computer animation is maintained while EEG responses are simultaneously being analyzed whereby the results of the analysis are then used to control the animation. EEG signals alone may be used to control computer animation and the EEG signals may be sent from the head of the user to a remote receiver by infrared wireless transmission.

U.S. Pat. No. 6,402,520 to Freer discloses a biofeedback system, an apparatus, incorporating EEF based biofeedback for improving attention. The system uses an educational protocol, which incorporates hierarchical master of skills, including visual discrimination, auditory discrimination, and/or sensory perception. The user practices attention growth while simultaneously attending to those factors which comprise perceptions and which thus affect attention.

These approaches are limited in what information is collected and how the brain state information is communicated to the wearer. Some of the limitations of these approaches include: single variable detection (e.g. EEG), context-dependence and location-dependence (e.g. used with video games and desktop computers). Existing feedback products use vibration or sound as a cue but lack fidelity and repeatability of notification as the body becomes desensitized to the stimulus after repetitive use.

Conventional approaches do not combine detection technology or feedback in a helpful manner. Some approaches use video games as a feedback mechanism. Generalizability of improved outcomes during a high stimulation video game environment to low stimulation environment, e.g. reading or listening has been questioned.

SUMMARY

The present subject matter focuses on skill improvement during a primary activity, thus weakening the generalizability argument. Executive function ("EF"), known to be crucial for school readiness, academic achievement and successful life outcomes, is a crucial state to be detected, trained and supported.

Executive function is a classification for a broad range of neurocognitive processes involved in goal-directed problem solving and self-control—processes such as cognitive flexibility, working memory, and inhibitory control. These processes can depend on the integrity of the prefrontal cortex; are related to, but distinct from IQ; and can be studied under the rubrics of effortful control, executive attention, and self-regulation.

EF skills can be fundamental for learning and achievement, including reading and mathematics; and predict learning success in high-risk children. Impairments in EF are a prominent feature of a number of psychiatric disorders with childhood onset including ADHD, conduct disorder, and autism, as well as specific problem behaviors such as physical aggression and substance abuse.

Although poor Executive Function (EF) is associated with problems in mental health and poor developmental outcomes, there is reason for optimism. EF skills are malleable and childhood years provide a window of considerable plasticity for change in this important domain, a time when EF normally improves markedly in conjunction with rapid brain development in the prefrontal cortex. Performance on measures of EF can be trained and curricula designed to foster the development of EF have also yielded promising results.

Age-related changes in EF can be the result of the extent to which children can recruit increasingly dorsal and anterior regions of prefrontal cortex into a hierarchical network of synchronized activation—a network that parallels the hierarchical structure of children's rule systems and develops in a bottom-up fashion, with higher levels in the hierarchy operating on the products of lower levels.

The recruitment of prefrontal regions is believed to be made possible by the iterative reprocessing of information in recurrent thalamocortical circuits that rely on increasingly high-frequency oscillations, measurable as resting EEG power in the Beta (15-30 Hz) and Gamma (~30-80 Hz) range. In general, research has shown that during childhood, activity in the slower frequency bands (e.g. delta) decreases while activity in the higher frequency (Alpha, Beta, Gamma) bands increases. These changes occurred during a period of marked growth in EF.

Providing direct ambulatory feedback on neural activity states correlated to EF could accelerate EF improvements and help sustain them in free-living conditions and during primary activities.

The present subject matter is in the technical field of neurofeedback and biofeedback. More particularly, the present subject matter is in the technical field of measurement and analysis of human neural and physiological states, and translation of these measurements into physical cues. These cues provide feedback to the individual to generate awareness, focus and attention. Once aware, an individual can actively direct their thoughts to cause improvements in cognitive learning including improved reading and listening, and behavioral interventions including strengthened emotional coping, improved social interaction and reduced stress and anxiety.

The present subject matter, by way of example, provides a wearable sensor that detects neural and/or physiological activity and compares the collected signals to recognized patterns of the same data that have been correlated to known mental, psychological and emotional states in previous studies and measurements. When the detected signal meets certain thresholds for significance it can be translated into physical cues that notify the wearer of a change in their current mental state. The wearer, once aware of their mental status, can choose to modify or sustain their current mental, psychological or emotional state using the device's cues to reinforce a change or to sustain a desired state. An additional visual cue can support the wearer if they need a guided approach to self-correct their mental state.

The present subject matter combines brain state and activity detection technologies with unique physical notification techniques to make the brain state detection technology more effective for applied behavior modification, therapy support and learning assistance. The present subject matter is portable and intended to be used in real-life situations outside laboratory and clinical settings.

BRIEF DESCRIPTION OF THE DRAWINGS

The drawings illustrate generally, by way of example, various embodiments discussed in the present document. The drawings are for illustrative purposes only and may not be to scale.

FIG. 5A shows an electro-optical liquid crystal lens system in which both lenses in the eyeglass frame are equally occluded reducing the transmissivity of the lenses with a clear area residing only in a small central area of the lenses, according to an example.

FIG. 5B shows an electro-optical liquid crystal lens system in which both lenses in the eyeglass frame are equally clear so as not to reduce the transmissivity of the lenses, according to an example.

DETAILED DESCRIPTION

An example provides a wearable sensor that detects neural and/or physiological activity. An example can compare collected signals to recognized patterns of data, such as data that have been correlated to mental, psychological and emotional states. Correlation can be established in studies or via measurements, such as measurements collected prior.

In an example, when a detected signal meets certain thresholds for significance it is then translated into physical cues that notify the wearer of their current mental state or of a change in their current mental state. The wearer, once alerted to their mental status, can modify or sustain their current mental, psychological or emotional state. Accordingly, the systems and methods provide cues to reinforce a change to, or sustaining of, a desired state. In an example, a visual cue, such as partially or totally occluded vision, can provide an indication to a wearer to provide a guided approach to self-correct their mental state.

An example combines brain state and activity detection with physical notification techniques to improve brain state detection such as to use in providing applied behavior modification, therapy support and learning assistance. An example can be worn by an ambulatory patient and can be used in real-life situations, such as outside laboratory and clinical settings.

Figure 1:
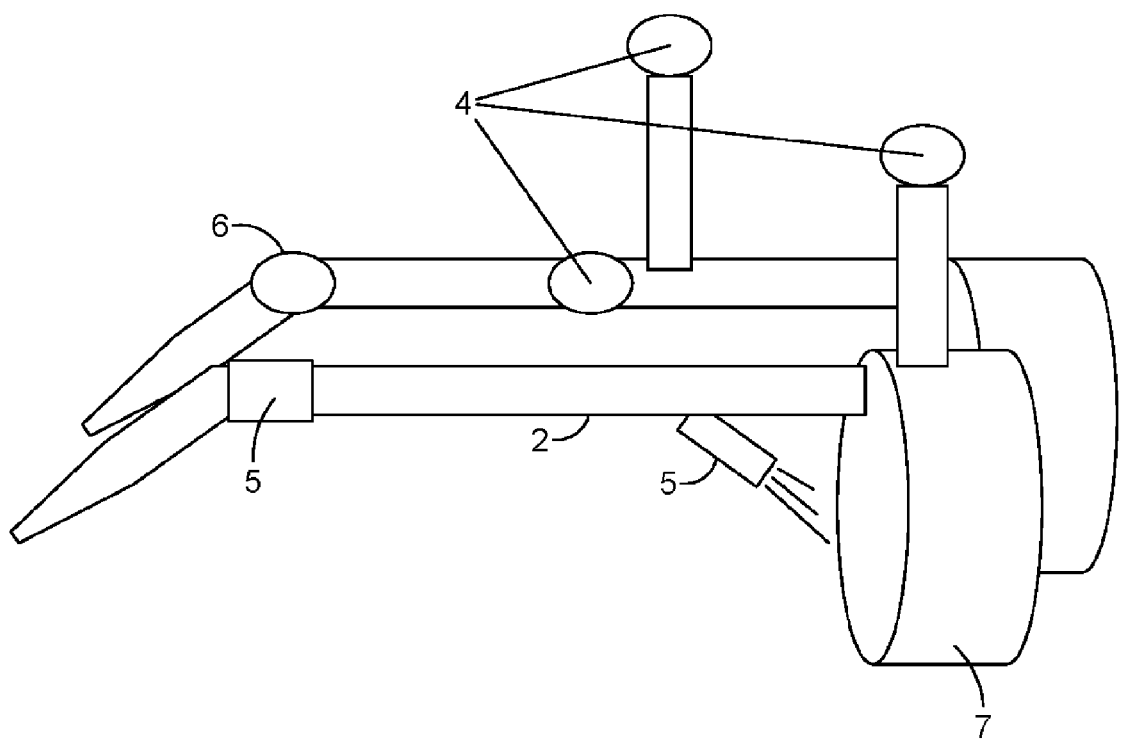
FIG. 1 illustrates an example of a device to detect and notify a wearer of mental states, such as in real-time during real-world tasks, according to an example.

FIG. 1 illustrates an example of a device to detect and notify a wearer of mental states, such as in real-time during real-world tasks. The device can include a headset or eyeglass portable chassis 2. A headset can include a wearable positioning apparatus such as a headband, such as for selective placement of electrode one or more sensors 4. An example includes an executive function training circuit 5. An example includes a sensory feedback stimulator 7, such as an eyeglass frame, containing electro-optical liquid crystal variable transmissivity lenses 7. A sensory feedback stimulator can include a stimulator to evoke perception using one or more somatosensory abilities, including, but not limited to, sight, sound, touch, pressure and sensitivity to heat, among others. A light projector 5 can be mounted on the frame 2 to emit a beam of light that is reflected on the back of the lenses 7.

An example includes one or more sensors 4 that can record neural activity in the form of brain waves. An example can route the data to the executive function training circuit 5. The executive function training circuit 5 can process the data, such as to detect a pattern. Based on the processed data, and example can generate a sensory feedback signal that controls the sensory feedback stimulation device, such as by controlling the transmissivity of the electro-optical liquid crystal lenses 7. Controlled selectable changes in the transmissivity of the electro-optical liquid crystal lenses can alter the amount of light viewed by wearer thus providing feedback and recognition of changes in executive function.

An example includes a power supply, such as mounted in bow of frame 2, such as to distribute power to one or more of: one or more sensors 4, executive function training circuit 5, a sensory feedback stimulator 6, such as electro-optical lenses 7 and any related data storage components associated with the executive function training circuit 5. In an example, connections and data transfer between various system device components occurs via conventional cabling or wiring. In an example, remote or wireless communications are conducted, such as via Wi-Fi, ZigBee, Bluetooth, IEEE 802.11a, IEEE 802.11b, IEEE 802.11g, IEEE 802.11n or other low power, short distance or near-field alternatives.

In an example, sensing, such as by one or more sensors 4, is based on at least one of electroencephalography (EEG), near-infrared reflectance spectroscopy (NIRS), functional near-infrared reflectance spectroscopy (fNIRS) or other brain state detection methodology. fNIR provides real-time monitoring of tissue oxygenation allowing quantitative assessment of brain functions—such as attention, memory, planning, and problem solving—while individuals perform cognitive tasks. fNIR measures NIR light absorbance in blood of hemoglobin with and without oxygen and provides information about ongoing brain activity similar to functional MRI studies. The fNIR device provides relative change in hemoglobin levels, calculated using a modified Beer-Lambert law.

In an example, one or more sensors 4 are located in a preselected pattern to sense neural activity in the form of different brain waves in different brain regions. In an example the executive function training circuit 5 can be embedded in the headset and can be communicated with, such as via a wireless network, smart phone technology or laptop computer. Accordingly, in an example, a executive function training circuit is split up and dispersed between a headset and glasses.

Figure 2:
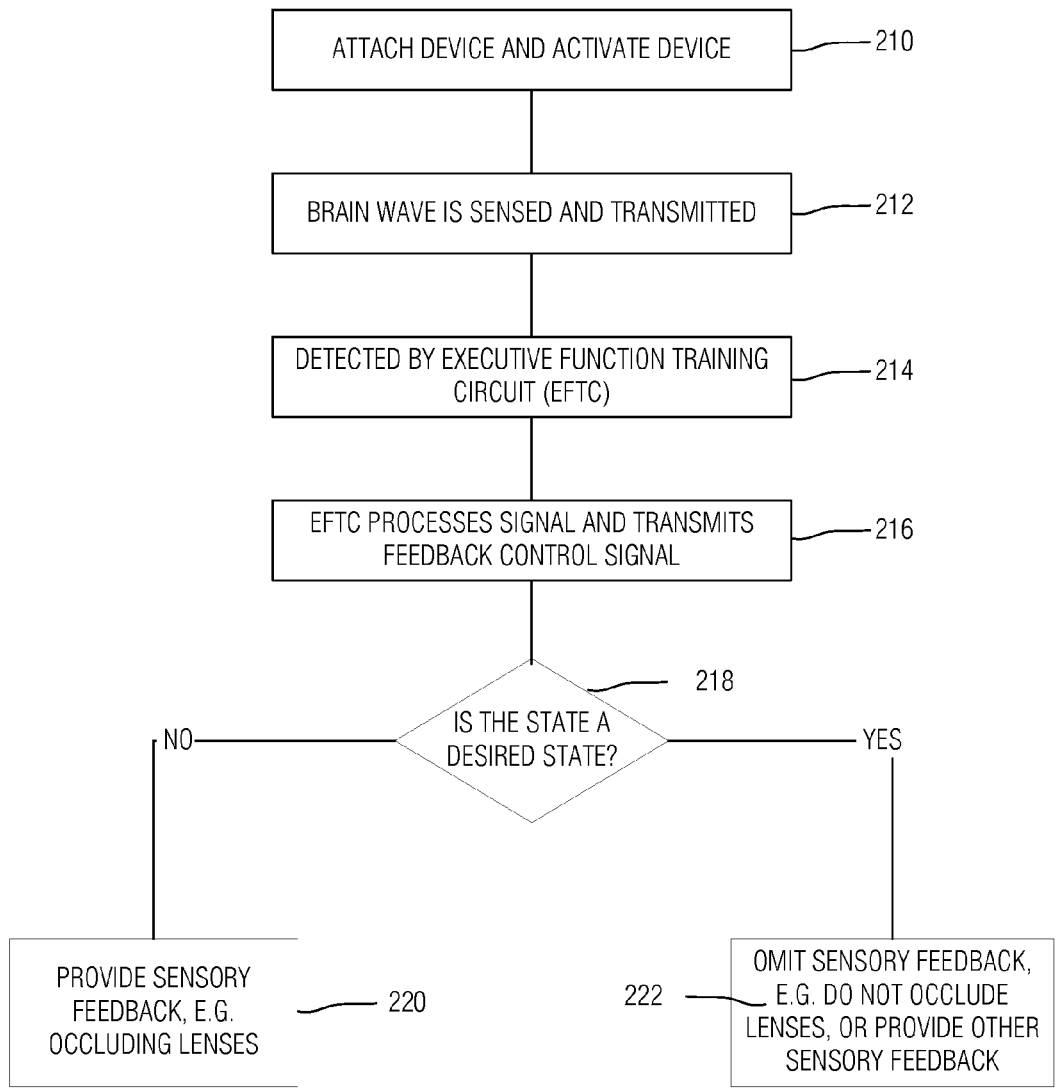
FIG. 2 is a process flow diagram of another example of the device, illustrating the functional relationships of the various system components, according to an example.

FIG. 2 is a process flow diagram of another example of the device, illustrating the functional relationships of the various system components. In an example, step 210 initiates the process with the placement and activation of a such a device 2. In an example, once activated, brain wave and state signals are sensed, preprocessed and transmitted in step 212, such as to an executive function training circuit. In an example, in step 214, executive function training circuit detects one or more signals. In an example, in step 216, the circuit processes them into appropriate control signals and determines control signals for sensory stimulation.

Algorithms to process and interpret signals such as electroencephalography (EEG) signals and translate said signals into the appropriate control signals for sensory stimulation, such as variable transmissivity lenses 7, can be preprogrammed into an executive function training circuit, and/or can be learned. In learned examples, a table is updated over time based on sensing performed by the device 2. For example, the device 2 is preprogrammed to recognize a successful alteration in EF, and records stimulation that resulted in the successful alteration of EF. In an example, algorithms for signal detection and translation are custom developed through training sessions that enable the initial devices to be preprogrammed with instructions executable to detect patterns and output associated feedback stimulus information. At 218, the method queries whether a desired state has been reached. If it has not, at 220 the method provides the sensory feedback stimulus. If the desired state has been reached, at 222 the method provides sensory feedback to confirm the desired state has been reached, or omits sensory feedback, such as by not occluding, or clearing lenses.

Figure 3:
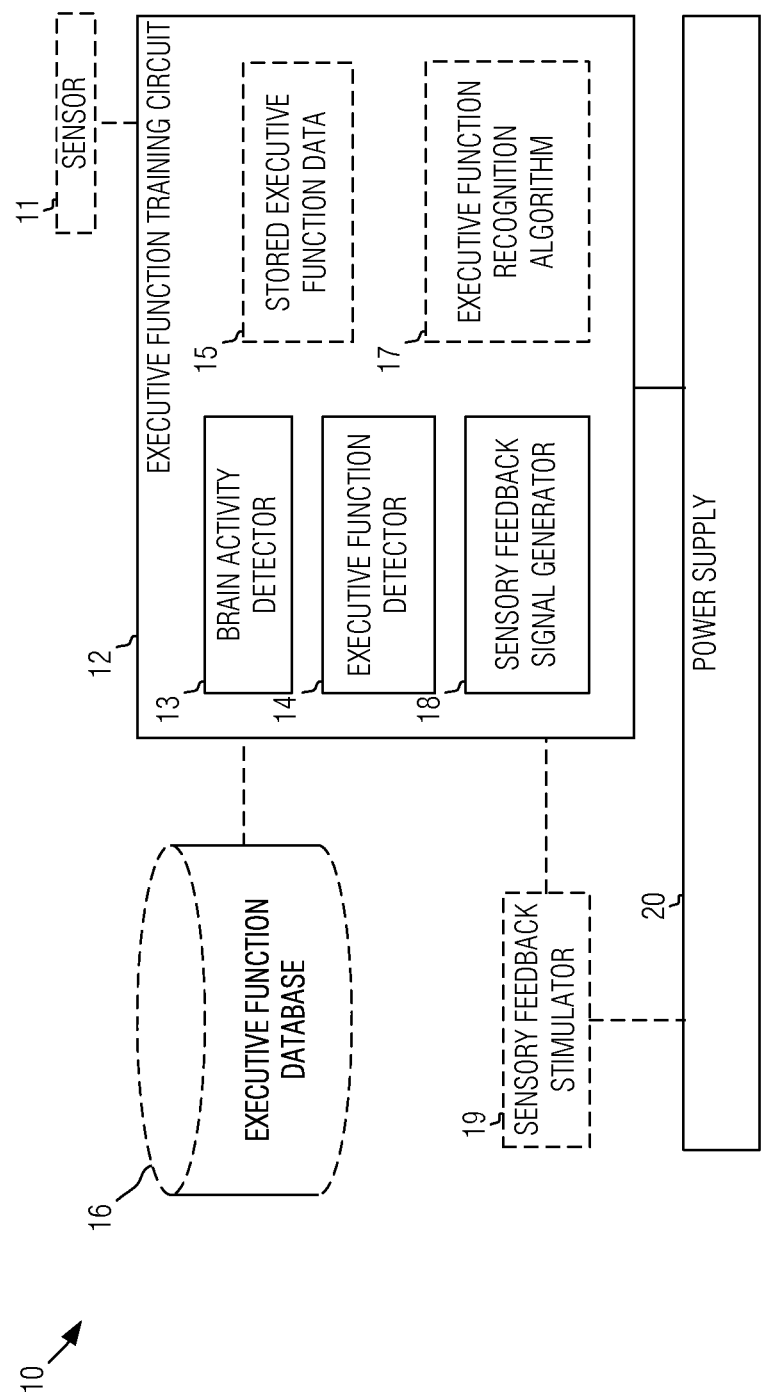
FIG. 3 is a high level layout of an example of the device, illustrating the functional relationships of subsystem components, according to an example.

FIG. 3 is a high level layout of an example of the device, illustrating the functional relationships of subsystem components. In an example, sensor 11 comprises one or more subsystem sensing components required for electroencephalography (EEG) brain state detection methodology, or other methodologies such as near-infrared reflectance spectroscopy (NIRS) and functional near-infrared reflectance spectroscopy (fNIRS). In an example, sensors are located strategically, such as to effectively sense neural activity in the form of different brain waves and states in different brain regions with initial emphasis on the frontal cortex region for the detection of executive function.

Executive function training circuit 12 consists of: brain activity detector 13, to detect the signals sent by the sensor 11; executive function detector 14 to process signals from the brain activity detector 13 so that they can be converted to critical executive function threshold levels; and a sensory feedback signal generator 18 to convert threshold levels to feedback signals sent to control the sensory feedback stimulator 19. An example enables translation of brain state data into effective sensory cues alerting the wearer to modify or sustain their current brain state.

An executive function training circuit 13 also enables exchange of undesired executive function data 15, stored in random access memory (RAM) and the undesired executive function database 16 with the executive function detector 14 for the purposes of processing and converting to critical executive function thresholds. In an example, one or more power supplies 20 are utilized to distribute power to the sensor 11, executive function training circuit 12, and the sensory feedback stimulator 19.

Figure 4:
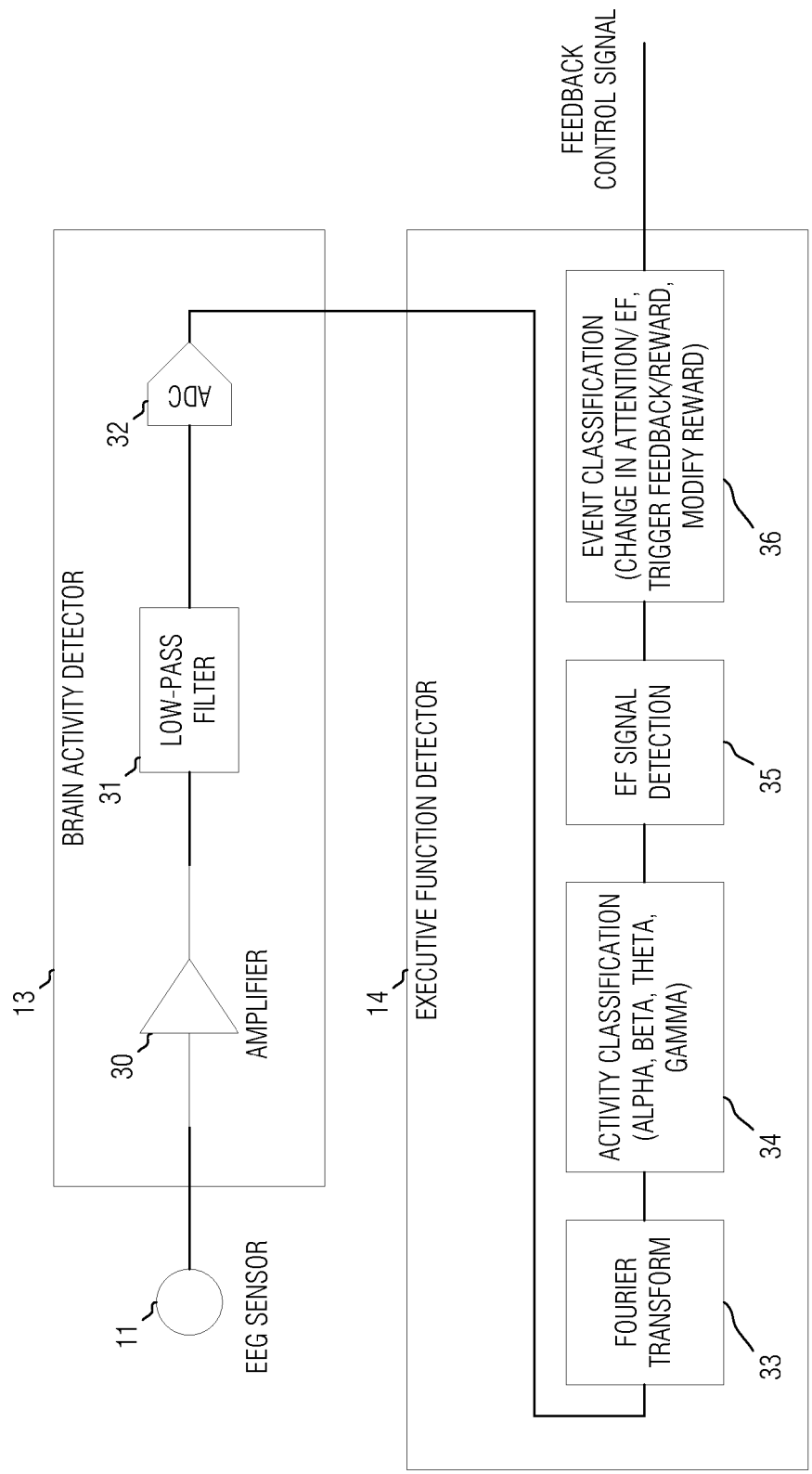
FIG. 4 is an example of the process signal flow from the neural sensor through the executive function training circuit using electroencephalography (EEG) sensors, according to an example.

FIG. 4 is an example of the process signal flow from the neural sensor 11 through the executive function training circuit 12 using electroencephalography (EEG) sensors. In an example, a signal is sent from sensor 11 to the brain activity detector 13. In an example, detector 13 includes an amplifier that is coupled to the sensor 11 in electrical communication with the sensor. The present subject matter optionally includes multiple sensors. In multiple sensor examples, for each sensor there may be a respective unique component of the detector 13.

In an example, the amplifier 30 is coupled to provide an amplified signal to a low-pass filter 31. In an example, the low pass filter 31 is coupled to provide a filtered signal to an analog-to-digital converter 32. The analog to digital converter is to provided a signal that has been converted to digital form. The digitized brain activity signal is then transmitted from the brain activity detector 13 to the executive function detector 14.

In an example, the executive function detector 14 includes one or more hardware and/or software components functions depicted therein. In an example, components perform a Fourier transform 33, such as by using a Fast Fourier Transform (FFT) algorithm, on one or more signals, such as to convert them spectral information. In an example, spectral information is classified into one or more of Alpha, Beta, Theta, and Gamma spectral information using an activity classification 34. In an example, an executive function ("EF") signal detection process 35 is performed to identify signals related to executive function. In an example, an event classification process 36 is performed by one or more hardware and/or software components, leading to identification of changes in attention or executive function that are related to triggering states to enable feedback, reward, and modified reward signals. This approach enables a feedback control signal to be sent to a sensory feedback stimulator such as a set of electro-optical liquid crystal lenses, a vibro-tactile device, an audio stimulation device, or some combination of the these devices.

In an example, sensor 11 measures one or more of brain wave activity, hemispheric and regional asymmetry of activity (e.g. more activity in Dorsolateral Prefrontal Cortex (DLPFC) or less activity in Anterior Cingulate Cortex (ACC), symmetry of brain region activity (e.g. ~40 hz Gamma synchrony, or general Alpha (8-12 hz) power) or other neural activity and generates a signal that is received and then sent to the executive function detector 14 for subsequent processing. In an example, increasingly high-frequency oscillations are measured prefrontal regions as resting electroencephalography (EEG) power in the Beta (15-30 Hz) and Gamma (~30-80 Hz) range. As set forth herein, neural activity is sensed by physical, optical or electrical sensors that detect a brain wave state or other neural condition. An example uses near-infrared reflectance spectroscopy (NIRS) sensors, or EEG and NIRS sensors in combination, or other brain state detection methodologies that can be made portable.

An example of an executive function detector processes the signals from the neural sensor 11 and brain activity detector 13, and compares the resulting processed signals to a pre-set signature or reference database pattern that indicates a distinctive brain state. In an example, each signal is processed to enable time averaging to reduce noise. In an example, signal analysis is performed in time or frequency space to evaluate correlation between signals. In an example, signals are filtered and/or triangulated to identify regional spatial source of most important signals.

An example of the present subject matter enables sensing and analysis of signals broader than just brain wave patterns (e.g., Alpha, Beta, delta, Gamma, Theta, sensorimotor rhythm (SMR) enhancement) that are normally measured. An example includes hemispheric asymmetry, symmetry of cross-region activity and other neural activity may also be measured and used to predict the wearer's accurate mental state in an example. An example correlates the changed cognitive skill (e.g. improved executive function) to improve reading and study skills and improved on-task performance in the classroom. In an example, training can induce pertinent brain states while reading, listening or interacting in other real-world applications. An example includes detection of other mental states to enhance cognitive and behavior skills (stronger impulse control, better coping with traumatic image, etc.) by providing a wearer with greater focus and attention on tangible external stimuli, such as stimuli other than mentally fabricated stimulus-independent thoughts.

An example of a signal processing approach includes the use of one or more sensors placed on the scalp of the individual in the area of the frontal cortex. In an example, each sensor detects one or more brain waves from different locations within the brain, such as with each wave containing information consisting of multiple amplitudes and frequencies. In an example, each sensor provides a complex time varying signal containing multiple amplitudes and frequencies. An example includes a headset with 14 sensors located on the scalp in the area of the frontal cortex.

An ambulatory example includes hardware and/or software components to identify one or more specific algorithms or processing approaches (e.g., comparing to stored baseline data) to be used on sensor signals. In an example, a device wearable by an ambulatory user includes a signal analyzer, signal conditioner, system controller, and power supply. In an example, components supporting the signal processing are located in a headset, in glasses, or split between locations in a manner the supports the proper processing and use of the signals while optimizing the weight and power distribution and human factors such as the user safety and friendliness of the device. In an example, if processor intensive filtering is to take place, a headset communicates information to a remote computer to perform the processing.

In an example, a pre-set signature or reference database pattern can be created using clinical trials or previous reference scans of the wearer that have been confirmed to correspond to distinctive mental states or are linked to known executive function patterns or some other cognitive capabilities (e.g. working memory, inhibition control, cognitive flexibility). In an example, high-power multi-channel laboratory electroencephalography (EEG) systems are used to determine accurate signatures. In an example, linkage of the electroencephalography (EEG) patterns with targeted behavioral conditions is done using industry accepted psychological assessments (e.g. National Institute of Health (NIH) toolbox neuropsychological tests). In an example, electroencephalography (EEG) signatures determined in clinical trials are loaded into devices of the present subject matter to serve as the reference database. In an example, when the measured state differs significantly from a pre-set desired state or matches the threshold of a desired reference pattern, depending on the effect desired, the device sends a signal to the Sensory Feedback Signal Generator 18 that triggers the Sensory Feedback Stimulator 19 to provide an observable physical sensory output that is perceived by the wearer.

An example communicates with a radio protocol to obtain data from the headset, one or both electroencephalography (EEG) and gyroscope data. An example performs frequency analysis of each electroencephalography (EEG) sensor channel, identifying artifacts associated with head movement. An example combines the measurements of Beta and Gamma power from individual sensors via a weighting scheme that will favor activity in the frontal scalp. An examples performs time averaging within a sliding time window. An example classifies the time time-averaged Beta and Gamma power based on criteria to be developed, and enable actuation the liquid crystal device (LCD) shutter mechanism to occlude subject vision according to their electroencephalography (EEG) activity score. In an example, communication with the radio protocol includes communicating commands to establish and maintain the wireless network with the headset, and to receive the streaming electroencephalography (EEG) and gyroscope data.

One example uses a low powered digital signal processor. Such a family of 16-bit fixed point digital signal processors offers low power (0.15 mW standby, 20 mW at 133 MHz) and a powerful 532 machine instructions per second in a quad-core processor. In this application the 16 electroencephalography (EEG) channels are sampled at 128 Hz. As an illustration of the capability of the digital signal processor, it is capable of performing 256-point complex fast Fourier transform (FFT) operations on all 16 channels at 128 Hz while still leaving 85% of the digital signal processors processing power available for other tasks.

In an example gyroscope data is analyzed to identify head movement. The headset features two gyroscopes oriented to be sensitive to changes in head azimuth (e.g., twisting left or right) and head pitch (e.g., nodding up or down). Raw gyroscope data is always accompanied with large static direct current (DC) offsets. These offsets vary from sensor to sensor and vary with temperature and time. A simple startup routine measures these offsets so that they can be subtracted from each data measurement. Thresholds are used to classify head movement. Thus, a measure of correlation between different head movements and their impact on the electroencephalography (EEG) data can be determined.

In an example Beta—(equation 1) and Gamma—(equation 2) power for each channel is obtained by summing the fast Fourier transform bins associated with the frequency range of interest (12-30, >30 Hz). This approach, summing fast Fourier transform (FFT) bins, offers considerable flexibility allowing additional filtering. For example, 60 Hz electrical interference can be removed by skipping the fast Fourier transform frequency (FFT) bins at 60 Hz. The individual Gamma power measured for each channel is obtained in this fashion. Total Gamma power is obtained via a weighted sum of the individual totals:

$$B_{total} = \sum_{channel\ i=1}^{16} w_i \beta_i \qquad (1)$$

-continued $$\Gamma_{total} = \sum_{channel\ i=1}^{16} w_i \gamma_i \qquad (2)$$

Where $\beta_i$, $\gamma_i$ represents, respectively, the Beta and Gamma power for electroencephalography (EEG) channel i and $w_i$ represents the weight between 0.0-1.0 reflecting the numerical estimate of the channels correlation to activity in the frontal cortex. In an example a collection of electroencephalography (EEG) data is made to obtain approximate values for these weights.

The quantities $B_{total}$, $\Gamma_{total}$ are updated at 128 Hz and filtered through an averaging algorithm to reduce the impact of noise, and are subjected to artifact removal based on head motion. The width of the averaging window is determined during this process and reflects the expected timescales associated with changes in attention and associated behaviors. The resulting time averaged power is classified to determine the appropriate neurofeedback response. The output of the classifier can be used to drive the liquid crystal device (LCD) shutter glasses electronics to create the desired reward.

Initial settings for contingent reward neurofeedback are based on increases in Beta or Gamma power relative to baseline, calibrated to provide approximately 5-10 "rewards" per minute. Criteria for reward is dynamic, however, and designed to "shape" increases in frontal power. Artifact rejection thresholds prevent feedback based on artifactual (e.g., movement-related) fluctuations. The development and calibration of training procedures, determination of thresholds to ensure the regimen can be comfortable and engaging for wearers, and evaluation of the utility of using the feedback modality are all verified during tests by a control set of wearers.

Electroencephalography (EEG) signatures determined in clinical trials can be loaded into the present subject matter to serve as the reference database. When the measured state differs significantly from a pre-set desired state or matches the threshold of a desired reference pattern, depending on the effect desired, the device sends a signal that triggers an observable physical sensory output that is perceived by the wearer. In an example, the desired or undesired mental reference patterns can be pre-set by the wearer depending on their intended use of the device, i.e. to improve attention, enhance relaxation, strengthen executive function skills, deal with trauma and intrusive thoughts, practice reflexive processing or control impulsive or addictive behavior. The device is thus tunable and amenable to multiple applications contrary to most existing devices.

In addition, an example of the detection step of the present subject matter utilizes supplementary physiological indicators to substitute for or complement the neurological measurements if cause-effect correlations and reaction times prove them to be adequate biofeedback signals. In an example, biofeedback measurements (e.g. pulse, skin conductance and skin temperature, heart rate variability etc.) are sensory correlates used to trigger the signal processor to notify the wearer of a change in mental state.

Visual impairment appears to be the sense least likely to be overridden by the body's sensory filtering mechanisms and to have the highest fidelity, effectiveness and sustainability. Impairing vision is believed to provide a high level of awareness of the detected mental state and encourage corrective action on part of the wearer. However, contemporary notification products lack the fidelity and repeatability of the present subject matter. Some examples use physical cues that can be overridden by the brain's sensory monitoring mechanisms and thus are of limited use for repeated notification. Use of the vibration mechanism of personal digital assistant (PDA) devices and phones are also limited in fidelity and repeatability of recognition of the cue by the wearer. According to examples discussed herein, eyeglasses transmissivity can be coupled to measures of prefrontal Beta and Gamma power. Other sensory cues can also be tested for efficacy, and long-term fidelity to alert the user of a change in brain state.

Electro-optic glasses are using liquid crystal technology to vary the transmissivity of the lenses. Glasses with different forms of adjustable variable transmissivity are described in U.S. Pat. Nos. 7,390,088; 7,344,244; 7,232,988; 3,423,149; 4,968,127; 5,015,086; 5,446,141; 5,608,567; 7,390,088 and 5,608,567; the specification of each of which is incorporated herein by reference in its entirety. FIG. 5 illustrates a embodiment of the Sensory Feedback Stimulator 19 in the form of an electro-optical liquid crystal lens system. In FIG. 5A both lenses in the eyeglass frame are equally occluded 100 reducing the transmissivity of the lenses with a clear area 101 residing only in a small central area of the lenses. In FIG. 5B both lenses in the eyeglass frame are equally clear 102 so as not to reduce the transmissivity of the lenses. Another example would enable that each lens in the eyeglass frame be independently controlled by sensory feedback control signals so that either lens could occlude different levels of the state of executive function.

Another example includes the variation of the overall contrast of each lens in an approximately uniform manner. Another example includes the outward distribution of the contrast from the center (e.g. radial distribution) of each lens, with the outer portion of each lens having higher transmissivity than the inner portions of the lens. An example controls changes in the level of contrast of each lens at some specific or customized spatial locations within the overall clear aperture area of the lenses.

In one example the signals from the sensors being wirelessly transmitted to a computer which serves as the signal detection device, a signal analyzer and conditioner, system controller, power supply, and wireless transmitter for a control signal sent to and received electro-optical glasses. The control signal being in the format necessary to control the transmissivity of electro-optical liquid crystal lenses.

In an example of the present subject matter, the lenses remain clear (e.g., completely transparent) when the desired or pre-programmed brain state from the reference database pattern is detected. In an example, the lenses occlude (e.g., varying levels of transparency) when an undesired brain state is detected that does not align with the targeted brain state pattern. These LCD based glasses allow the lenses to rapidly change from transparent to relatively opaque (and vice versa) under electronic control.

Some examples of devices include electro-optical variable transmission eye-glasses newly entering the marketplace due to the ongoing development of 3D televisions and commercial display systems. The technologies would require slight modifications to the format and packaging concepts to efficiently integrate the previously described system components of a portable executive function feedback device where changes in Gamma power, or other measured EF-correlated brain wave states, would elicit predictable changes in transparency levels.

An additional example of a device assists the wearer in proactively intervening in changing their mental state by using a visual dot projected on the inner portion of the lenses of the eyeglasses that prompts the wearer to follow the dot as it is randomly projected in different quadrants. This activity requires the wearer to move away from mind-wandering, reliving traumatic events, engaging in compulsive behavior or giving into strong impulses. This embodiment is based on Eye Movement Desensitization and Reprocessing (EMDR) therapy developed by Dr. Francine Shapiro. EMDR has shown benefits for Posttraumatic Stress Disorder PTSD sufferers (and other psychological disorders) to help them interrupt traumatic flashbacks or intrusive thoughts and bring the patient back to a state of present awareness and self-control and lessen their symptoms. The present subject matter incorporates EMDR and EEG-biofeedback therapies into a device which can be used outside a therapy session to reinforce and strengthen the wearer's coping skills and reinforce the gains made in clinical therapy and supervised training sessions.

Detection of brain wave activity has been described in U.S. Pat. Nos. 6,402,520; 5,377,100 5,595,488, 5,983,129; 6,167,298 6,450,820 6,097,981; 6,402,520; 6,626,676; and 6,947,790; the specification of each of which is incorporated herein by reference in its entirety.

Two additional novel forms of exogenous physical stimuli may also be included in the present subject matter as notification cues. A cue based on biomimicry principles incorporates the tactile sensory experience of a crawling insect, slithering worm or other ecological phenomenon and is hypothesized to have the highest fidelity of recognition and lowest risk of being overridden compared to other arbitrary or artificial cues (e.g. vibration, sound). The evolutionary survival significance of this natural stimuli suggests it will not be overridden as readily as artificial stimuli. This stimulus is a modification of the formication or paresthesia phenomena noted in the literature.

One example of sensory notification may occur via vibromechanical tactile stimulation where a series of sequentially firing vibromechanical stimulators vibrating against a suitably tactile sensitive surface of the wearer, such as skin, to induce a phenomenon of illusion of linear continuity. This illusion of linear continuity, through vibromechanical stimulators tapping on the suitably tactile sensitive surface of the wearer, can be used to produce simple or complex pattern configurations. One example is the formication or paresthesia phenomena noted in the literature. Simulation of the third-party tickle (e.g., Knismesis-light tickle, Gargalesis-heavy tickle) response is also a physical stimuli with high fidelity that can be added to the present subject matter to increase fidelity of notification.

Figure 6:
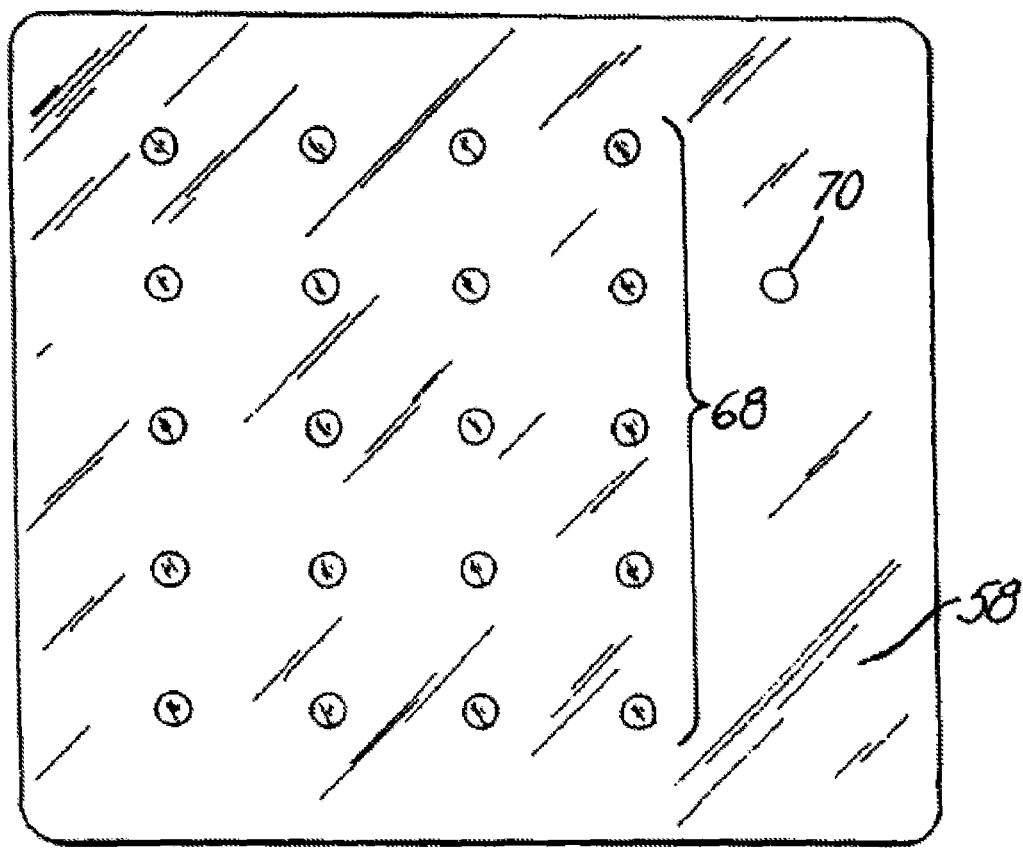
FIG. 6 shows twenty-one housing face apertures with twenty in a housing face aperture array that is four columns of five apertures, according to an example.
Figure 7:
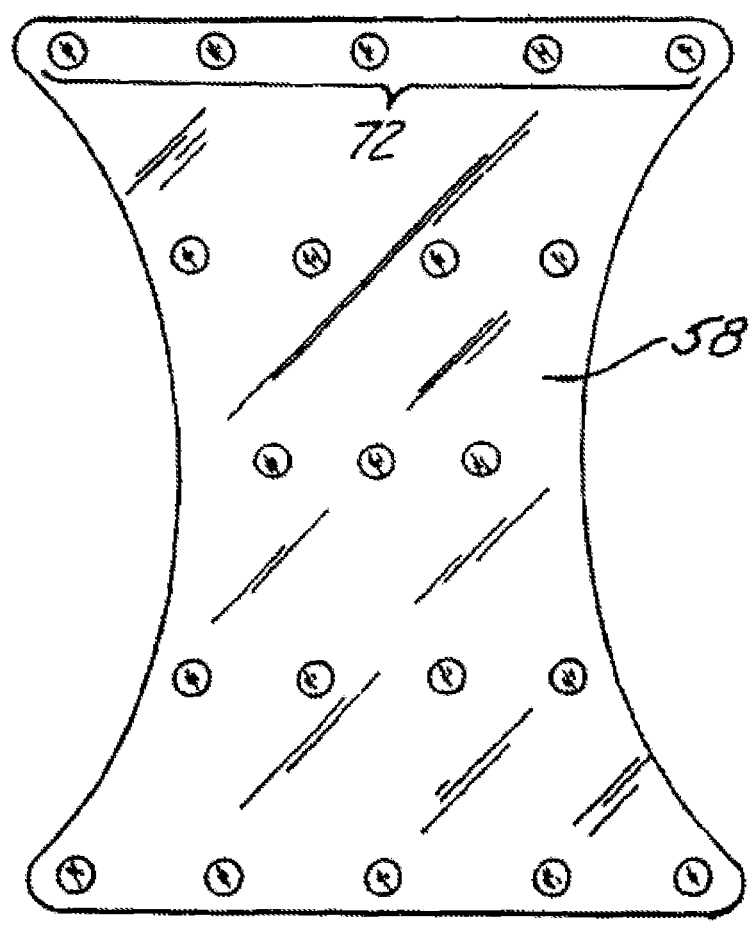
FIG. 7 depicts an embodiment using twenty-one apertures in a housing face aperture array having the shape of an hourglass in its two dimensional configuration, according to an example.
Figure 8:
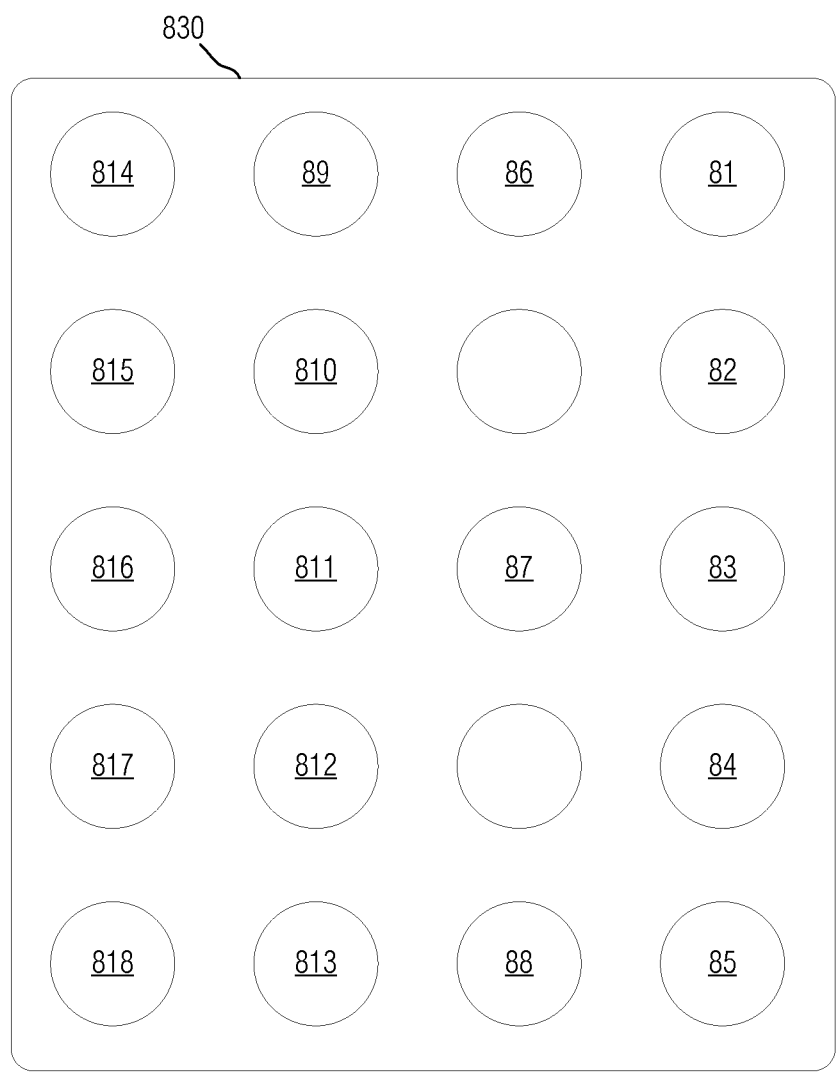
FIG. 8 shows sensors numbered to depict a firing of an array of sensory stimulators, according to an example.

In an example each vibromechanical stimulator is triggered to vibrate individually and sequentially from one stimulator to the next successive stimulator for the pattern chosen to be conveyed. FIGS. 6-8. The array includes a plurality of vibromechanical stimulators positionable in a substantially two dimensional array, positioned over a suitable tactile sensitive surface area of the human and the plurality of vibromechanical stimulators being connected to the power source. A control circuit is connected to the power source and to the tactile stimulator array for independently and sequentially controlling each vibromechanical stimulator.

FIGS. 6 and 7 represent two embodiments for conveying patterns. The present subject matter provides many different two dimensional arrays of stimulators are available both in spatial orientation and in total numbers of stimulators used. Stimulators can include shock electrodes, vibromechanical and the like. Portions of the present subject matter are discussed in U.S. Pat. No. 6,326,901, the specification of which is incorporated herein by reference in its entirety. For example, as depicted in FIG. 6, there are twenty-one housing face apertures with twenty in a housing face aperture array 68 that is four columns of five apertures. There is an additional aperture 70 placed to the side of aperture array 68 as an asymmetric configuration providing this embodiment with an aperture array capable of employing the asymmetric aperture 70 within the complete array or alternatively using aperture 70 and its corresponding stimulator to provide an asymmetric stimulus that may carry additional meaning. An example might be triggering the stimulator through aperture 70 to indicate that the tactile communication device is about to begin a message transmission, or switch from alphabet to numeric or even possibly denote when the next character to be delivered is a known complex pattern alerting the wearer to pay a heightened level of attention to the next character so as to discern its true nature. Further use of an asymmetric aperture such as aperture 70 is discussed herein.

FIG. 7 depicts an embodiment using twenty-one apertures in a housing face aperture array 72 having the shape of an hourglass in its two dimensional configuration. This particular arrangement depicted by aperture array 72 was arrived at through studies to determine the most efficient two dimensional array pattern for being able to trace all the letters of the English alphabet and the complement of Arabic numerals as discussed below. Depiction of these three aperture arrays in no way should be construed as a limitation in the actual number of useful two dimensional arrays available to the present invention. Although not disclosed, additional two dimensional patterns have been studied and useful arrays have been constructed from patterns employing as few as nine stimulators to as many as thirty. Arrays utilizing from fifteen to twenty-three stimulators have demonstrated the greatest practicality in terms of highest efficiency at the lowest cost and still providing accurate rendition of the received message.

FIG. 8 is numbered to depict the sequential actuating of an array of eighteen (18) stimulators using the array pattern to generate the numbers 0 through 9. This particular array is convenient for generating letters as well as numbers. As used, tactile communication device 830 is inverted over the skin of a wearer such that the pattern traced on the skin will be normal to the person's perception but will be necessarily inverted if one were to look directly at an array. One of the possible sequences for generating the number "1" by sequentially actuating the stimulators associated with electrodes labeled 81, 82, 83, 84 and 85. The pattern that is traced begins with actuating the stimulator associated with electrode 81 individually and then sequentially followed by stimulator at electrode number 82, then at 83, then at 84, and finishing at 85. The number "2" is traceable using the following actuating sequence of 82, 86, 89, 815, 811, 87, 84, 85, 88, 813, and ending with electrode 818. The number "3" has the actuating sequence of 81, 86, 89, 814, 810, 87, 812, 818, 813, 88 and 85. The number "4" uses sequential actuating of two linear patterns. The first sequential actuating begins with 81 and continues with 82, 83, 87, 811 and ends with 816. The number "4" pattern is then completed with the second sequence actuating beginning with 9, then 810, 811, 812, and ending with 813. Note that the stimulator associated with electrode 811 is used at two different times during the pattern tracing. A actuating sequence useful for the number "8" beginning with electrode 816, then going through the sequence 815, 814, 89, 86, 81, 82, 83, 87, 811 and returning to 816. Firing 816 a third time, the sequence then continues through 817, 818, 813, 88, 85, 84, 83, 87, 811, and finally back to 816. As is seen, the stimulator at electrode 816 has been used three times and the three stimulators at electrodes 83, 87 and 811 were used twice.

The pattern trace for the number "9" begins at electrode 814 and progresses through electrodes 9, 86, 81, 82, 83, 87, 811, 816, 815, and then 814 again. 814 then communicates again after its slight delay and the sequence finishes through 815, 816, 817, ending at 818. The number "9" might just as easily have been generated in a linear fashion, for example by inverting the "6" pattern. The pattern approximate how these numbers are written by hand. Recognition and accuracy have been shown to improve when construction of the patterns can follow the actual tracings one might use to create the numbers on paper.

As should be understood, the present invention is not necessarily limited to such a strict representation. An example of a useful alternative pattern may be found where only two stimulators are employed to convey the number zero. The number zero is traced by beginning with the stimulator at electrode 85, then jumping to 814 and then actuating number 85 for a second time. It is understood that the wearer of the tactile communication device would necessarily need to know that this particular pattern represented the number zero. One obvious alternative is to program a stimulator sequence actuating sufficient to draw out a zero.

Audible signals may also be used as a stimulation cue to the wearer. One example would have the audio delivered through an ear bud inserted into the ear. The ear bud would deliver a tone when signaled by the neurofeedback stimulator.

In addition to the non-obvious and novel visual impairment modality and tickle and insect-crawling stimuli mentioned above other examples of the wearer notification step of the present subject matter could manifest as different observable physical outputs that include audio, tactile, scent or varying visual cues or combinations of the foregoing to effectively and repeatedly notify the wearer of their current mental state.

Upon repeated usage of the present subject matter to detect and notify wearer of changing brain states the wearer becomes attuned to and proficient in how to adjust their brain state using the direct neurofeedback. In an example, the device can be useful for strengthening attention skills, inducing relaxation, controlling rumination and mind-wandering and providing greater levels of cognitive flexibility, self-control and impulsivity management which should strengthen executive function skills. Improvement in these areas can lead to lowered stress, greater control of certain psychological disorders, improved classroom performance and behavior, and generally improved cognitive skills and elevated well-being.

Figure 9:
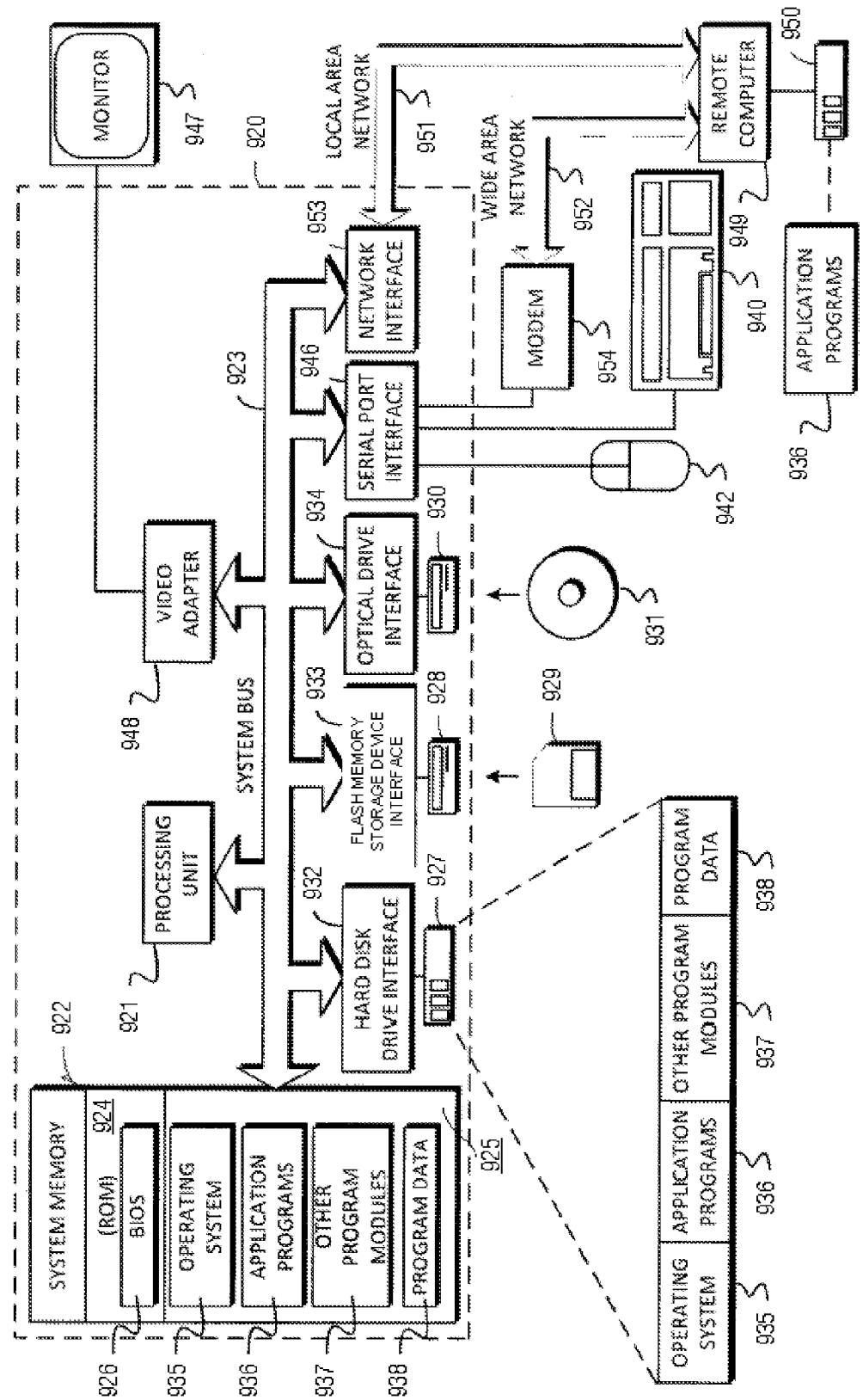
FIG. 9 is a block diagram of a computer system to implement methods according to an example embodiment, according to an example.

FIG. 9 is a block diagram of a computer system to implement methods according to an example embodiment. Examples such as method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

In the embodiment shown in FIG. 9, a hardware and operating environment is provided that is applicable to processing components in the circuits and controllers disclosed here, including the sensory feedback generator circuit. As shown in FIG. 9, one embodiment of the hardware and operating environment includes a general purpose computing device in the form of a computer 900 including one or more processing units 921, a system memory 922, and a system bus 923 that operatively couples various system components including the system memory 922 to the processing unit 921. There can be only one or there can be more than one processing unit 921, such that the processor of computer 900 comprises a single central-processing unit (CPU), or a plurality of processing units, commonly referred to as a multiprocessor or parallel-processor environment.

The system bus 923 can be any of several types of bus structures including a memory bus or memory controller, a peripheral bus, and a local bus using any of a variety of bus architectures. The system memory can also be referred to as simply the memory, and, in some embodiments, includes read-only memory (ROM) 924 and random-access memory (RAM) 925. A basic input/output system (BIOS) program 926, containing the basic routines that help to transfer information between elements within the computer 900, such as during start-up, can be stored in ROM 924. The computer 900 can include a hard disk drive 927 for reading from and writing to a hard disk, not shown, a flash memory storage device 928 for reading from or writing to a removable flash memory storage device 929, and an optical disk drive 930 for reading from or writing to a removable optical disk 931 such as a CD ROM or other optical media.

The hard disk drive 927, flash memory storage device 928, and optical disk drive 930 couple with a hard disk drive interface 932, a flash memory storage device interface 933, and an optical disk drive interface 934, respectively. The drives and their associated computer-readable media provide non volatile storage of computer-readable instructions, data structures, program modules and other data for the computer 900. It should be appreciated by those skilled in the art that any type of computer-readable media which can store data that is accessible by a computer, such as magnetic cassettes, flash memory cards, digital video disks, Bernoulli cartridges, random access memories (RAMs), read only memories (ROMs), redundant arrays of independent disks (e.g., RAID storage devices) and the like, can be used in the exemplary operating environment.

A plurality of program modules can be stored on the hard disk, flash memory storage device 929, optical disk 931, ROM 924, or RAM 925, including an operating system 935, one or more application programs 936, other program modules 937, and program data 938. Programming for implementing one or more processes or method described herein can be resident on any one or number of these computer-readable media.

A user can enter commands and information into computer 900 through input devices such as a keyboard 940 and pointing device 942. Other input devices (not shown) can include a microphone, joystick, game pad, satellite dish, scanner, or the like. These other input devices are often connected to the processing unit 921 through a serial port interface 946 that is coupled to the system bus 923, but can be connected by other interfaces, such as a parallel port, game port, or a universal serial bus (USB). A monitor 947 or other type of display device can also be connected to the system bus 923 via an interface, such as a video adapter 948. The monitor 947 can display a graphical user interface for the user. In addition to the monitor 947, computers typically include other peripheral output devices (not shown), such as speakers and printers.

The computer 900 can operate in a networked environment using logical connections to one or more remote computers or servers, such as remote computer 949. These logical connections are achieved by a communication device coupled to or a part of the computer 900; the invention is not limited to a particular type of communications device. The remote computer 949 can be another computer, a server, a router, a network PC, a client, a peer device or other common network node, and typically includes many or all of the elements described above input/output relative to the computer 900, although only a memory storage device 950 has been illustrated. The logical connections depicted in FIG. 9 include a local area network (LAN) 951 and/or a wide area network (WAN) 952. Such networking environments are commonplace in office networks, enterprise-wide computer networks, intranets and the internet, which are all types of networks.

When used in a LAN-networking environment, the computer 900 is connected to the LAN 951 through a network interface or adapter 953, which is one type of communications device. In some embodiments, when used in a WAN-networking environment, the computer 900 typically includes a modem 954 (another type of communications device) or any other type of communications device, e.g., a wireless transceiver, for establishing communications over the wide-area network 952, such as the internet. The modem 954, which can be internal or external, is connected to the system bus 923 via the serial port interface 946. In a networked environment, program modules depicted relative to the computer 900 can be stored in the remote memory storage device 950 of remote computer, or server 949. It is appreciated that the network connections shown are exemplary and other means of, and communications devices for, establishing a communications link between the computers can be used including hybrid fiber-coax connections, T1-T3 lines, DSL's, OC-3 and/or OC-12. TCP/IP, microwave, wireless application protocol, and any other electronic media through any suitable switches, routers, outlets and power lines, as the same are known and understood by one of ordinary skill in the art.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

The present subject matter encompasses several examples. Example 1 includes a system for training an ambulatory user, the system comprising: an executive function training circuit configured to couple with a user-wearable electrical sensor, the executive function training circuit comprising: a brain activity detector configured to receive electrical signals from a user-wearable electrical sensor and detect one or more brain activities; an undesired executive function detector configured to detect one or more executive function portions of the one or more brain activities attributable to an undesired executive function; and a sensory feedback generator configured to provide a training signal to a sensory feedback stimulator in association with the detection of the one or more executive function portions of the one or more brain activities attributable to an undesired executive function.

Example 2 includes the system of example 1, wherein the executive function training circuit is to couple to an electroencephalograph recorder, and the electrical signals include an electroencephalograph.

Example 3 includes the system of any one of examples 1-2, wherein the executive function training circuit is to couple to a functional near-infrared imager, and the electrical signals include a functional near-infrared image.

Example 4 includes the system of any one of examples 1-3, wherein the executive function training circuit is to provide the training signal to one or more of a group including a set of lenses with variable transmissivity, a speaker and a vibrator.

Example 5 includes the system of example 3, wherein the sensory feedback generator is configured to determine an effective duration and magnitude for transmissivity reduction and to reduce transmissivity in association with a determined effective duration and magnitude.

Example 6 includes the system of example 4, wherein the sensory feedback generator is configured to provide a voltage signal to electro-active lenses to alter transmissivity.

Example 7 includes the system of any one of examples 1-6, wherein the executive function training circuit is battery powered, and configured to power both the user-wearable electrical sensor and the sensory feedback stimulator.

Example 8 includes the system of any one of examples 1-7, wherein the executive function training circuit is disposed in an eyeglasses frame.

Example 9 includes the system of any one of examples 1-8, wherein the executive function training circuit is disposed in a portable electronic device.

Example 10 includes the system of any one of examples 1-9, wherein the brain activity detector is configured to detect brain activities associated with one or more of a group including spatial activities and temporal activities, and the undesired executive function detector is configured to correlated the one or more of a group including spatial activities and temporal activities one or more of a group including high levels of executive function, low levels of executive function, alertness, mind wandering and rumination.

Example 11 includes a method of training an ambulatory user, the method comprising: sensing electrical signals; detecting brain activity from the electrical signals; analyzing the brain activity and detecting executive function from the brain activity; detecting whether the brain activity is an undesired brain activity attributable to an undesired executive function; and if the brain activity is attributable to an undesired executive function, providing a sensory feedback.

Example 12 includes the method of example 11, comprising: determining whether to correct for the undesired executive function; if the undesired executive function is to be corrected for, providing a correction indication; and providing the sensory feedback in association with the correction indication.

Example 13 includes the method of any one of examples 11-12, wherein detecting brain activity includes detecting one or more of a group including anatomical location, amplitude and synchrony of one or more of a group including Gamma, Alpha, Beta and Theta frequency brain waves.

Example 14 includes the method of any one of examples 11-13, wherein the sensory feedback is provided in real-time, immediately following detection of whether the brain activity is an undesired brain activity attributable to an undesired executive function.

Example 15 includes the method of any one of examples 11-14, wherein the sensory feedback is provided independent of an additional stimulation.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A system for training an ambulatory user, the system comprising:
   a user-wearable device;
   one or more variably transmissive lenses coupled to the user-wearable device;
   a user-wearable electrical sensor coupled to the user-wearable device;
   an executive function training circuit configured to couple with the user-wearable electrical sensor, the executive function training circuit comprising:
      a brain activity detector configured to receive electrical signals from the user-wearable electrical sensor and detect one or more brain activities;
      an undesired executive function detector configured to detect one or more executive function portions of the one or more brain activities attributable to an undesired executive function; and
   a sensory feedback generator operatively coupled to the variably transmissive lenses and configured to provide feedback to the user regarding the undesired executive function by impairing the vision of the user through the one or more lenses through by reducing the transmissivity of the one or more variably-transmissive lenses.

2. The system of claim 1, wherein the executive function training circuit is coupled to an electroencephalograph recorder, and the electrical signals include an electroencephalograph.

3. The system of claim 1, wherein the executive function training circuit is coupled to a functional near-infrared imager, and the electrical signals include a functional near-infrared image.

4. The system of claim 1, wherein the executive function training circuit is configured to also provide feedback to the user using one or more of a group including a speaker and a vibrator.

5. The system of claim 1, wherein the one or more variably transmissive lenses include two variably-transmissive lenses, and the sensory feedback generator is configured to impair the vision of the user through both eyes by reducing the transmissivity of both of the variably-transmissive lenses.

6. The system of claim 1, wherein the one or more variably-transmissive lenses include electro-active lenses, and the sensory feedback generator is configured to provide a voltage signal to the one or more variably-transmissive lenses to alter transmissivity.

7. The system of claim 1, wherein the executive function training circuit is battery powered, and configured to power both the user-wearable electrical sensor and the sensory feedback generator.

8. The system of claim 1, wherein the executive function training circuit is disposed in an eyeglasses frame.

9. The system of claim 1, wherein the executive function training circuit is disposed in a portable electronic device.

10. The system of claim 1, wherein the brain activity detector is configured to detect brain activities associated with one or more of a group including spatial activities and temporal activities, and the undesired executive function detector is configured to correlate the one or more of a group including spatial activities and temporal activities with one or more of a group including high levels of executive function, low levels of executive function, alertness, mind wandering and rumination.

11. A method of training an ambulatory user using one or more electrically- controllable lenses positioned near one or both eyes of the user, the method comprising:
   sensing electrical signals from the user using a user-wearable electrical sensor;
   detecting brain activity from the electrical signals;
   analyzing the brain activity and detecting executive function from the brain activity;
   detecting whether the brain activity is an undesired brain activity attributable to an undesired executive function; and
   when the brain activity is attributable to an undesired executive function, impairing the vision of the user through the one or more lenses by sending an electrical signal to the electrically-controllable lenses to modify an optical quality of the one or more lenses by reducing the transmissivity of the one or more lenses, wherein impairing the vision of the user provides sensory feedback to the user about the brain activity attributable to an undesired executive function.

12. The method of claim 11, wherein the impairing the vision of the user interrupts the reception of visual information by the user.

13. The method of claim 11, wherein detecting brain activity includes detecting one or more of a group including anatomical location, amplitude and synchrony of one or more of a group including Gamma, Alpha, Beta and Theta frequency brain waves.

14. The method of claim 11, wherein impairing the vision of the user includes impairing the vision of the user substantially immediately following detection brain activity attributable to an undesired executive function, wherein feedback is provided to the user in real-time.

15. The method of claim 11, wherein the sensory feedback is provided independent of an additional stimulation.

16. The method of claim 11, wherein modifying an optical quality of the one or more lenses includes occluding at least one of the or more lenses.

17. The method of claim 11, wherein modifying an optical quality includes changing the lenses from transparent to substantially opaque.

18. A neurosensing and feedback system comprising:
a user-wearable device;
one or more electrically-controllable lenses, at least one variably transmissive lens coupled to the user-wearable device and configured to be positioned in front of both the eyes of a user, the one or more electrically-controllable lenses configured to modify a variable optical quality of the one or more electrically-controllable lenses;
a sensor system, at least a portion of the sensor system mounted on the user-wearable device, the sensor system configured to sense neural activity in the form of brain waves ;
a feedback circuit configured to communicate provide feedback to the user by impairing the vision of the user through the electrically-controllable lenses with the user wearable device, the feedback circuit comprising:
a brain activity detector configured to receive electrical signals from the sensor system and convert the electrical signals into one or more digital signals and detect one or more brain activities;
a brain activity analyzer configured to receive the one or more digital signals from the brain activity detector and process the one or more digital signals to one or more brain activities and identify one or more brain activity patterns that is associated with an undesired executive function; and
a sensory feedback controller generator configured to send a control signal to the one or more electrically-controllable lenses to modify the variable optical quality of the electrically-controllable lenses vary the transmissivity of at least a portion of the least one variably transmissive lens in association with the brain activity analyzer identifying the one or more activity patterns. the identification of the one or more brain activity patterns, and wherein the one or more electrically-controllable lenses are variably-transmissive lenses, and the feedback circuit impairs the vision of the user by reducing the transmissivity of the one or more electrically-controllable lenses.

19. The neurosensing and feedback system of claim 18, wherein the neurosensing and feedback system is configured to train the user to maintain attention to a cognitive task, the brain activity analyzer being configured to detect a change in attention to the cognitive task, and the sensory feedback controller is configured to modify the variable optical quality of the electrically-controllable lenses in response to detection by the brain activity analyzer of the change in attention to the cognitive task.

* * * * *

UNITED STATES PATENT AND TRADEMARK OFFICE
CERTIFICATE OF CORRECTION

PATENT NO. : 9,510,765 B2  
APPLICATION NO. : 13/989536  
DATED : December 6, 2016  
INVENTOR(S) : Rod Greder Page 1 of 1

It is certified that error appears in the above-identified patent and that said Letters Patent is hereby corrected as shown below:

In the Claims

In Column 19, Line 20, in Claim 16, after "the", insert --one--, therefor

In Column 19, Line 36, in Claim 18, delete "waves ;" and insert --waves;--, therefor In Column 20, Line 20, in Claim 18, delete "patterns." and insert --patterns,--, therefor Signed and Sealed this  
Ninth Day of February, 2021

Drew Hirshfeld  
*Performing the Functions and Duties of the*  
*Under Secretary of Commerce for Intellectual Property and*  
*Director of the United States Patent and Trademark Office*